United States Patent
Kruse et al.

(10) Patent No.: US 6,881,224 B2
(45) Date of Patent: Apr. 19, 2005

(54) FATIGUE TEST FOR PROSTHETIC STENT

(75) Inventors: Steven D. Kruse, Bloomington, MN (US); Chad Q. Cai, Woodbury, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 44 days.

(21) Appl. No.: 10/034,694

(22) Filed: Dec. 28, 2001

(65) Prior Publication Data

US 2003/0125804 A1 Jul. 3, 2003

(51) Int. Cl.$^7$ ................................................ A61F 2/24
(52) U.S. Cl. .................... 623/2.11; 73/37; 73/865.6
(58) Field of Search .............................. 623/2.11, 2.13, 623/913; 73/865.6, 37

(56) References Cited

U.S. PATENT DOCUMENTS

| | | | |
|---|---|---|---|
| 4,343,048 A | | 8/1982 | Ross et al. |
| 4,778,461 A | * | 10/1988 | Pietsch et al. ............. 623/2.19 |
| 5,176,153 A | * | 1/1993 | Eberhardt .................... 128/897 |
| 5,272,909 A | * | 12/1993 | Nguyen et al. ................. 73/37 |
| 5,406,857 A | * | 4/1995 | Eberhardt et al. .......... 73/866.4 |
| 5,531,094 A | * | 7/1996 | More et al. ................... 73/1.72 |
| 5,571,174 A | | 11/1996 | Love et al. |
| 5,584,878 A | | 12/1996 | Love et al. |
| 5,662,705 A | | 9/1997 | Love et al. |
| 5,670,708 A | * | 9/1997 | Vilendrer ....................... 73/37 |
| 5,899,937 A | * | 5/1999 | Goldstein et al. ........... 623/2.11 |
| 5,961,549 A | | 10/1999 | Nguyen et al. |
| 6,165,216 A | | 12/2000 | Agathos |
| 6,171,335 B1 | | 1/2001 | Wheatley et al. |
| 6,245,105 B1 | | 6/2001 | Nguyen et al. |
| 6,562,069 B1 | * | 5/2003 | Cai et al. .................... 623/2.12 |

FOREIGN PATENT DOCUMENTS

| | | |
|---|---|---|
| WO | WO02/065952 | 8/2002 |

* cited by examiner

*Primary Examiner*—Corrine McDermott
*Assistant Examiner*—Thomas J Sweet
(74) *Attorney, Agent, or Firm*—Westman, Champlin & Kelly, LLC (57) ABSTRACT

An improved method for testing a stent for a prosthetic valve includes applying a load with a fluid against a stented test structure in a backward direction with the stented test structure substantially blocking the flow of the fluid. The stented test structure includes a stent and a flexible membrane extending within the lumen defined by the stent with the flexible membrane having a plurality of contours connecting to the stent along the scallops. A corresponding testing apparatus includes a cyclic pressure applicator, a conduit connected to the cyclic pressure applicator, and a stented test structure mounted within the conduit to receive cyclic fluid pressures from the cyclic pressure applicator. The stented test structure includes a stent and a flexible membrane extending within the lumen defined by the stent. The flexible membrane substantially blocks flow of the fluid in a backward direction and does not fully open upon application of the fluid pressure in a forward direction.

33 Claims, 9 Drawing Sheets

FATIGUE TEST FOR PROSTHETIC STENT

FIELD OF THE INVENTION

The invention relates to methods for the testing of stents, i.e., leaflet support structures, used for valved prostheses, especially heart valve prostheses. In particular, the invention relates to stent fatigue testing using hydraulic forces.

BACKGROUND OF THE INVENTION

Physicians use various prostheses to correct problems associated with the cardiovascular system, especially the heart. For example, the ability to replace or repair heart valves with prosthetic devices has provided surgeons with a method of treating heart valve deficiencies due to disease and congenital defects. A typical procedure involves removal of the native valve and surgical replacement with a prosthetic heart valve.

Prosthetic heart valve leaflets or occluders perform the function of opening and closing to regulate blood flow through the heart valve. Typically, heart valve leaflets must either pivot or flex with each cycle of the heart to open and close. Heart valves function as check valves, which open for flow in one direction and close in response to pressure differentials.

Prostheses can be constructed from natural materials such as tissue, synthetic materials or a combination thereof. Prostheses formed from purely synthetic materials can be manufactured, for example, from biocompatible metals, ceramics, carbon materials, such as graphite, polymers, such as polyester, and combinations thereof. Heart valve prostheses with purely synthetic materials can be manufactured with rigid occluders or leaflets that pivot to open and close the valve, or flexible leaflets that flex to open and close the valve.

Although mechanical heart valves with rigid pivoting occluders have the advantage of proven durability through decades of use, they are associated with blood clotting on or around the prosthetic valve and thromboembolism. Blood clotting can lead to acute or subacute closure of the valve. For this reason, patients with mechanical heart valves remain on anticoagulants for as long as the valve remains implanted. Anticoagulants have associated risks and cannot be taken safely by certain individuals.

Heart valve prostheses with flexible leaflets can be constructed with tissue leaflets or polymer leaflets. In prostheses with flexible leaflets, the leaflets function similarly to natural leaflets. While the leaflets are flexible, they must have a well defined and stable configuration to properly open and close the valve at each cycle in response to pressure differentials. Also, the leaflets should be durable to provide stable performance over many years of use.

Unlike mechanical valves, tissue based bioprostheses do not require the long term use of anticoagulants due to a lower incidence of thromboembolism. While tissue leaflets have desired flexibility and acceptable hemodynamic performance, tissue leaflets can calcify after implantation, which results in loss of flexibility, resulting in improper closure and/or opening of the valve. For individuals with appropriate indications, tissue-based heart valve prostheses provide practical alternatives to mechanical heart valve prostheses.

Valve prostheses with polymer leaflets have the potential to overcome the shortcomings of both tissue and mechanical valve designs. The polymers incorporated into heart valve prostheses should provide long term stable function to be suitable alternatives for tissue leaflets or mechanical valve leaflets.

SUMMARY OF THE INVENTION

In a first aspect, the invention pertains to a method for testing a stent for a prosthetic valve. The method includes applying a fluid pressure against a stented test structure in a backward direction with the stented test structure substantially blocking the flow of the fluid. The stented test structure includes a stent and a flexible membrane extending within the lumen defined by the stent. The flexible membrane does not fully open upon reversal of the fluid pressure applied in a forward direction.

In another aspect, the invention pertains to a testing apparatus comprising a cyclic pressure applicator, a conduit connected to the pressure applicator, and a stented test structure mounted within the conduit to receive cyclic fluid pressures from the pressure applicator. The stented test structure includes a stent and a flexible membrane extending within the lumen defined by the stent. The flexible membrane substantially blocks flow of the fluid in a backward direction and does not fully open upon reversal of the fluid pressure in a forward direction.

In a further aspect, the invention pertains to a stented test structure including a stent and a flexible membrane extending within the lumen defined by the stent. The stent includes a plurality of commissure posts and scallops extending between the commissure posts. The flexible membrane connects to the stent along the scallops and opens no more than about 80 percent of the full open lumen at the edge of the stent corresponding to the inflow edge of the prosthesis upon application of fluid pressure in a forward direction.

DETAILED DESCRIPTION OF THE INVENTION

A new fatigue testing procedure for stents of prosthetic valves, especially heart valve prostheses, involves hydraulic testing using the stent in association with a flexible membrane connected to the stent which transfers a load from the fluid to the stent. The flexible membrane generally differs from conventional leaflets in that the flexible membrane does not fully open or does not open at all when fluid pressure is applied to a stented test structure in a forward direction, which would correspond with the direction from the inflow edge to the outflow edge of a prosthetic valve mounted on the stent. Since the flexible membrane does not fully open for fluid flow, the stented test structure can be cycled at a higher frequency than a corresponding heart valve prosthesis. The hydraulic testing loads transferred to the stent more closely approximate the type of loading on the stent in vivo following implantation. Thus, a more accurate evaluation of the fatigue of the stent can be performed.

Valved prostheses have flexible leaflets that open and close in response to pressure changes. In particular, damaged or diseased native heart valves can be replaced with valved prostheses to restore valve function. In embodiments with flexible leaflets, the leaflets function similarly to native tissue leaflets. Suitable heart valve prostheses can be designed as a replacement for any heart valve, i.e., an aortic valve, a mitral valve, a tricuspid valve, or a pulmonary valve. In addition, valved prostheses can be used for the replacement of vascular valves, although for convenience, the discussion herein focuses primarily on heart valve prostheses. The patient can be an animal, especially a mammal, and preferably is a human.

The flexible leaflets of the valve are configured to flex in response to changes in blood flow. In particular, the valves generally function as one way check valves that fully open to allow flow in a forward direction and close in response to pressure applied in a backward direction. Similar to leaflets of a prosthetic valve, the membrane substantially blocks fluid flow when fluid pressure is applied in the backward direction, which is generally opposite to the forward direction defined above. In other words, the backward direction corresponds with the direction from the outflow edge to the inflow edge of a prosthetic valve mounted on the stent. When the valve closes in response to pressure differentials, the free edges of adjacent leaflets contact in the closed configuration with the leaflets extending across the lumen. In the closed position, the leaflets eliminate or greatly reduce back flow through the valve. The contacting portion of the leaflets is referred to as the coaptation region.

Heart valve prostheses with flexible leaflets generally have leaflets formed from tissue or polymers. Tissue-based valved prostheses can include harvested natural valves or components thereof, or tissue portions that are assembled into appropriate valve components. The tissue can be autograft tissue, allograft tissue or xenograft tissue. The tissue, especially xenograft tissue, can be fixed using a crosslinking agent.

Polymer leaflets are formed from a thin film of flexible polymer. Suitable polymers are biocompatible, in that they are non-toxic, non-carcinogenic and do not induce hemolysis or an immunological response. Heart valve prostheses formed from polymers preferably are non-thrombogenic. Relevant mechanical properties of polymers include, for example, stiffness, strength, creep, hardness, fatigue resistance and tear resistance. Preferred polymers are durable in that they do not significantly lose their flexibility and do not significantly lose their mechanical strength following many years of use.

In a prosthetic valve with flexible leaflets, the leaflets are supported by a support structure. In stentless valve embodiments, the support structure is not sufficiently rigid to maintain the leaflet function of the valve against the forces opening and closing the valve. In embodiments of particular interest herein, the support structure includes a sufficiently rigid component that maintains the leaflet function of the valve against the forces opening and closing the valve. In particular, the support structure is sufficiently rigid to prevent valve collapse against the fluid pressures closing the valve. Valves with a rigid support structure are termed stented valves, and the sufficiently rigid support is called a stent. The stent provides a scaffolding for the leaflets. Since the stent is rigid, only the base of the stent is necessarily attached to the patient or other device. As a particular example, heart valve stents are used to support leaflet components within a prosthetic heart valve.

Stents generally include commissure posts and scallops that extend between commissure posts. The commissure posts support the free edges of the leaflets while the scallops support the fixed edges of the leaflets. The scallop shape allows the attachment of a leaflet with sufficient freedom of motion to move from a fully closed position to a fully open position. As long as the stent provides for the appropriate support of the leaflets along the commissure posts and scallops, the stent can be formed with a range of designs from, for example, a thin wire-form or a sheath shape that fills in all or a portion of the regions between the scallops. In addition to the stent, a sewing cuff, fabric cover and/or other non-support elements can be included with the prosthesis to facilitate implantation of the valve and/or handling of the valve.

The edge of the prosthesis at or near the lower portion of the stent below the scallops forms the inflow edge of the valve. Generally, the stent, the sewing cuff and/or other structure together form a generally annular structure between the scallops and the inflow edge. The other edge of the valve opposite the inflow edge is the outflow edge. Flow through the corresponding prosthesis incorporating the stent goes through the central lumen of the valve. The leaflets can be attached to the stent using any of a variety of fastening approaches. For example, the leaflets can be fastened using suture, staples, adhesives or the like. Polymer leaflets can be formed around the stent to form an integral unit.

Valved prostheses are generally intended for long term use following implantation. Replacement of heart valve prostheses requires a surgical procedure with its associated risks, and failure of the prosthesis can place the patient at risk. Thus, testing of the components of the prosthesis is important to ensure that the valve will perform in a satisfactory fashion following implantation. Furthermore, regulatory agencies require testing as a part of the approval process for a prosthesis. Testing can also be a significant aspect of the design process for the production of improved prostheses with desirable performance characteristics.

Testing may involve several different aspects. Durability testing for leaflets can be performed by mounting a completed valve in an accelerated wear tester. Separate fatigue testing of the stents can be used to evaluate the performance of the stents independent of the leaflets.

Stents are subject to considerable loads after implantation of the prosthesis due to fluid forces on the leaflets. The loads reach a maximum when the prosthetic valve is in a closed position. The stent keeps the valve from collapsing against the force of the fluid pressing against the closed leaflets. One testing approach for the stent alone involves mechanical contact with the tips of the commissure posts to deflect the commissure posts to an amount observed under mock physiological conditions. While the displacement of the post tip may be similar to that observed in a pulse duplicator system, the application of the load to the stent during this mechanical fatigue testing can be distinctly different from the load transferred from the leaflets to the stent when a pressure load is applied to a closed valve by the fluid. Maximum stress levels in the stent under a physiological load transferred from the leaflets to the stent can be significantly different than a point load applied to the tips of the stent to deflect the stent tips a similar amount. The relationship between the stress applied by mechanical post deflection and load transfer through a membrane under fluid pressures can vary considerably with stent design. Similarly, mechanical deformation of the stent tips generally does not reproduce the distribution of the load. Thus, the load magnitude and overall deformation of the stent resulting from tip displacement may not correspond with the magnitude and distributions of the load transferred through leaflets to the stent in vivo.

In contrast, the improved stent testing procedures described herein involves a hydraulic process using the stent with a flexible material membrane attached to the stent to transfer the load from the fluid to the stent. The flexible membrane attached to the stent to perform the testing of the stent may have different mechanical properties than leaflets of the prosthesis, although the membrane generally has similar geometry and elasticity as leaflets in a valve. Unlike valve leaflets, the testing membrane does not fully open to allow flow through the valve lumen under test conditions. The preferred testing approaches herein involve the transfer of a load from a fluid to the stent that more closely approximate in magnitude and/or in distribution the loads applied in the corresponding prosthesis after implantation. The magnitude of the load may depend on the frequency at which the fluid is cycled, although the fluid pressure can be adjusted to compensate for these frequency dependant variations in the magnitude of the load.

The test apparatus to perform the stent fatigue testing involves the stented test structure, a mount for the stented test structure and a hydraulic system or cyclic pressure applicator to cycle the stented test structure with a fluid. The stented test structure includes the stent, a flexible membrane within the central lumen of the stent and, optionally, mounting structures, such as a sewing cuff, to facilitate the mounting of the stented test structure on the testing apparatus mount. The mount generally involves a tubular element or the like that surrounds the base of the stent to direct fluid pressures within the central lumen of the stented test structure such that there is little or no leakage of fluid around the outer portion of the stented test structure. A pump or other means of applying cyclic pressures can be used to apply the load to the stent for the testing. Suitable cyclic pumps include, for example, a Harvard-style piston pump, a cam actuated piston pump or other cyclic pump designs. In other embodiments, oscillating centrifugal forces or a continuous pump with periodic valve functions can be used to produce cyclic fluid pressures.

The stented test structure maintains fluid on both sides of the flexible membrane of the stented test structure. The fluid generally is liquid on the downstream (backward pressure generating) side of the stented test structure and may be liquid or gas, such as air at atmospheric pressure, on the upstream side of the stented test structure. While the flexible membrane may not allow flow, the orientation of the structure can be referenced relative to the upstream and downstream directions of a corresponding valve with leaflets mounted on the stent. For the performance of the stent fatigue test, fluid pressure is applied in a backward direction from the downstream side of the stented test structure with a selected magnitude and temporal variation While the flexible membrane of the stented test structure has a closed configuration approximating the closed position of the leaflets of the corresponding prosthetic valve, the flexible membrane in preferred embodiments has significant differences from the leaflets. In particular, the flexible membrane generally does not open to a fully open position when appropriate fluid pressure is applied in a forward direction to provide for flow through the central lumen. The flexible membrane can be partially sealed to limit the flow and/or the material of the flexible membrane can be sufficiently less flexible than the leaflet material so that the flexible membrane does not open up fully at the pressures used for testing. In some embodiments, the flexible membrane is sealed across the valve lumen to prevent any significant flow through the stented test structure as the fluid cycles the structure.

In preferred embodiments, the material used to form the flexible membrane in the stented test structure has an elasticity, i.e., in plane extensibility, comparable to the leaflet material of the valve prosthesis such that the load transferred to the stented test structure is approximately comparable in magnitude and in distribution as the load transferred by the leaflets in the corresponding prosthesis. With respect to leaflets, to achieve the desired flexibility of the leaflets and to reduce resistance to forward flow, the leaflets are thin. However, since the flexible membrane does not flex to a fully open configuration, the membrane does not have to be as flexible as the leaflets. In general, elasticity of a piece of membrane material is inversely proportional to its elastic modulus and thickness, while its flexibility is inversely proportional to the elastic modulus and the thickness to the third power. If the membrane material has lower elastic modulus than the leaflet, it can be made thicker to have similar elasticity to the leaflet, but it will be less flexible.

While the leaflets of a prosthetic valve are necessarily durable, fatigue testing of the stent inherently entails pushing the stent structure near its limits. It is not desirable to have durability of the flexible membrane compromise the testing of the fatigue properties of the stent. Since the membrane does not have to be as flexible, the membrane can be made more durable. Increased durability can be introduced through one or more approaches. For example, the flexible membrane of the stented test structure can include additional reinforcements and the like that do not significantly alter the elasticity while improving the durability. Furthermore, different materials can be used to form the flexible membrane than are suitable for leaflets both because of the reduced need for flexibility and because the flexible material does not need to be biocompatible. Additionally, or alternatively, the material can be made thicker as long as the elasticity is not inappropriately altered.

If the flexible membrane of the stented test structure is formed from tissue, the tissue can be reinforced at stress points, such as the commissure posts, to improve the durability of the material. In addition, the tissue can be sutured or otherwise fastened across a portion or all of the free edges of the coapting leaflets to keep the leaflets from fully opening. In addition, somewhat thicker tissue material can be used without significantly altering the transfer of the load to the stent.

In some preferred embodiments, the flexible membrane is formed from a polymer. The polymer can be extruded, cast, molded, calendered or the like to form the membrane. In some preferred embodiments, the polymer membrane is formed by placing the stent onto a mandrel and then dip coating the mandrel into an appropriate polymer liquid. The polymer is then solidified on the stent to form the stented test structure. In this way, the polymer membrane is formed as an integral unit with the stent and is removed from the mandrel as a unit. The mandrel is shaped to correspond approximately with the closed configuration of the corresponding valve prosthesis. The top of the mandrel can include sharp edges at selected locations to separate any free edges of the membrane at those selected locations to provide for desired amounts of flow through the polymer structure. Alternatively, the polymer can be cut along its top edge to form partial free edges in the polymer membrane. Reinforcements can be included in the polymer material to make the membrane more durable.

Thus, the stent testing approaches described herein can provide a more accurate test of a stent in which the forces on the stent more closely approximate the physiological forces on the stent during valve function. At the same time, by forming the flexible membrane such that it does not fully open, the testing can be done at high cycling rates within a practical testing time for an appropriate number of cycles that is comparable to the cycling times used with mechanical post deflection test. The apparatuses for performing the stent testing can be constructed or adapted from presently available components and apparatuses.

Valved Prostheses And Stents

The testing procedures described herein can be used for testing stents to be incorporated into valved prostheses. In particular, the stented valves can be used in artificial hearts, heart valve prostheses, valved vascular prostheses or left ventricular assist devices.

While the embodiments of the valved prosthesis shown in the figures below have three leaflets, valved prostheses can be constructed with different numbers of leaflets, such as one leaflet, two leaflets, four leaflets or more than four leaflets. The prosthesis may or may not have the same number of leaflets as the natural valve that it is used to replace. The number of leaflets dictates the structure of the corresponding stent since the stent supports the edges of the leaflet.

Heart valve prostheses are suitable for the replacement of damaged or diseased native heart valves. Mammalian hearts have four major valves. With appropriate sizing and attachment, the prosthetic valves are suitable for replacement of any of the heart valves. In particular, heart valve prostheses for replacement of the mitral and tricuspid valves generally include rigid stents although some embodiments allowing for chordae attachment may be stentless. Similarly, embodiments of aortic valves and pulmonary valves may also include stents.

Mammalian veins include valves that assist with blood circulation by limiting the amount of back flow in the veins. Veins collect blood from capillaries and are responsible for returning blood to the heart. Generally, vascular valves are replaced as part of a vascular graft with sections of conduit. The stented valve prostheses can be incorporated into a vascular graft with a conduit for replacement of a venous valve or for the replacement of an aortic or pulmonary heart valve. In addition, a stented valve, as described herein, can be incorporated into a left ventricular assist device.

Figure 1:
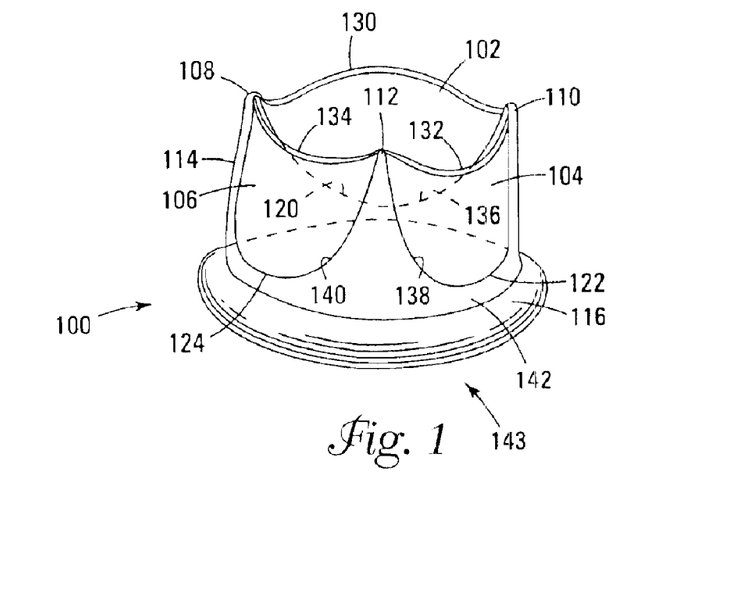
FIG. 1 is a perspective view of a stented heart valve prosthesis with flexible leaflets in an open position.
Figure 2:
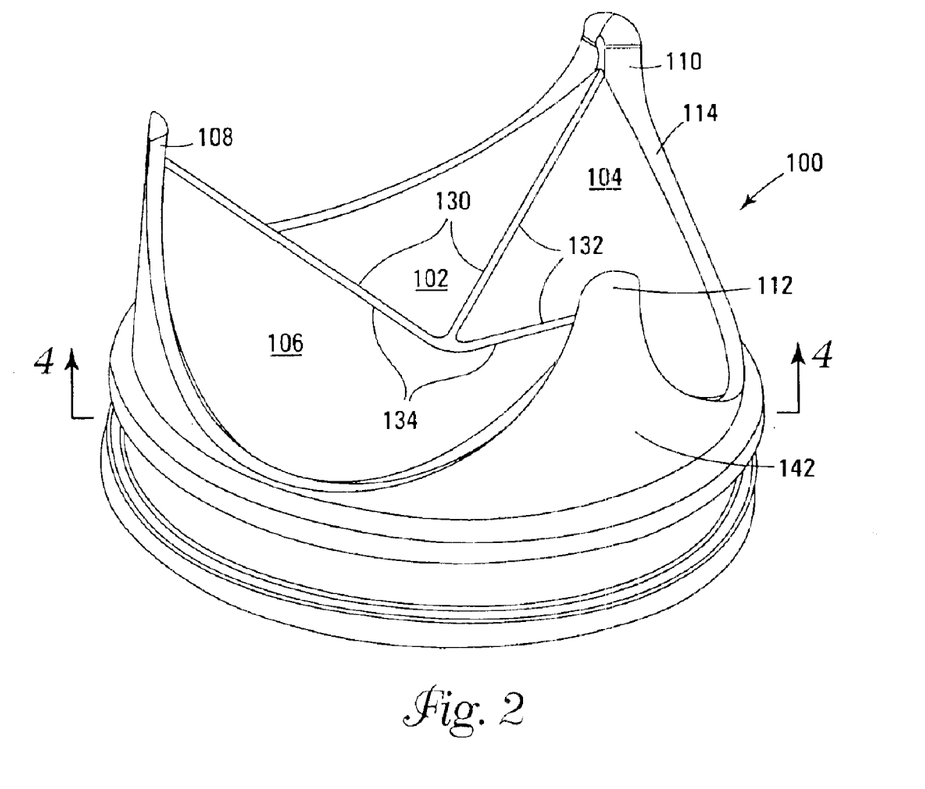
FIG. 2 is a perspective view of a stented heart valve prosthesis with flexible leaflets in a closed position.
Figure 3:
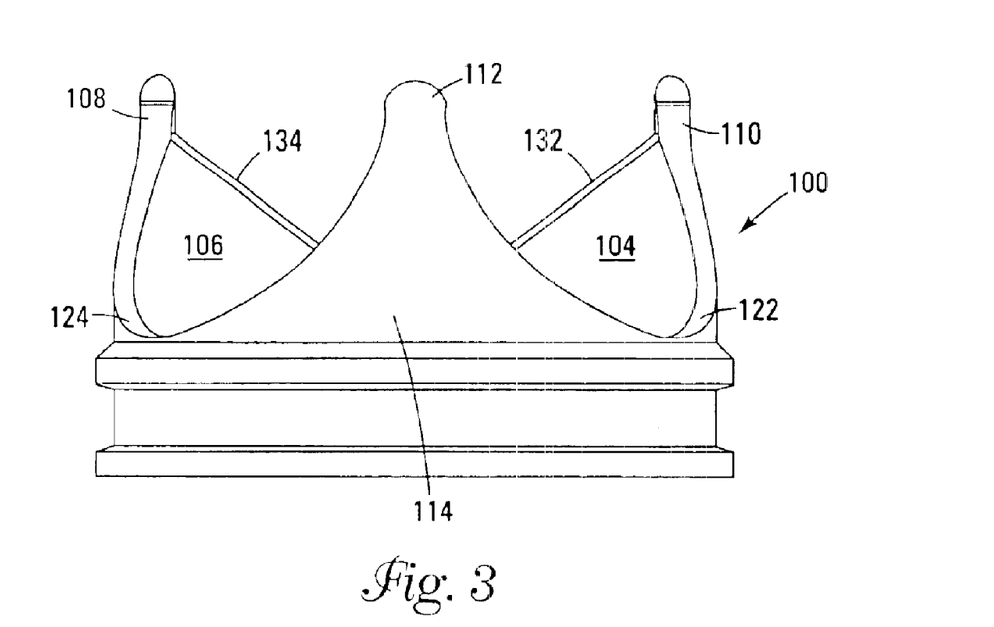
FIG. 3 is a side view of the heart valve prosthesis of claim FIG. 2.
Figure 4:
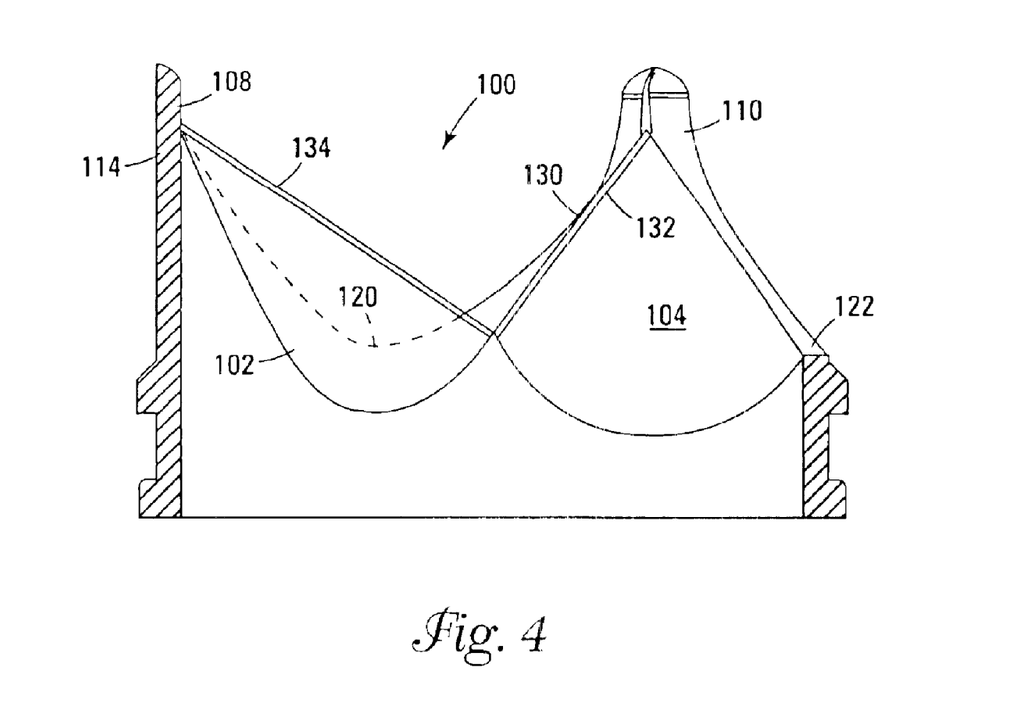
FIG. 4 is a sectional side view of the heart valve prosthesis of FIG. 2 taken along line 4—4 of FIG. 2.

An embodiment of a stented heart valve prosthesis with flexible leaflets is shown in its fully open position in FIG. 1. Heart valve prosthesis 100 includes leaflets 102, 104, 106, support structure/stent 114 and sewing cuff 116. Heart valve prosthesis 100 with closed leaflets is shown in FIGS. 2–4. Leaflets 102, 104, 106 contact the respective adjacent leaflets to close the valve.

Sewing cuff 116 is used to attach valve 100 to the patient's tissue annulus or to other portions of a prosthesis. In embodiments of interest, support structure/stent 114 is relatively rigid, such that the support structure functions as a stent to maintain leaflet function with attachment to the patient only at base 142 of stent 114. Stent 114 includes commissure supports 108, 110, 112 and scallops 120, 122, 124 between the commissure supports. Free edges 130, 132, 134 of leaflets 102, 104, 106, respectively, join at the commissure supports 108, 110, 112. Attached edges 136, 138, 140 of leaflets 102, 104, 106 also secure to the stent 114 along scallops 120, 122, 124. The base 142 of stent 114 generally has the shape of a cylindrical ring or the like that forms the opening into the valve at the upstream or proximal end 143 of the valve.

Sewing cuff 116 generally extends from base 142 of stent 114. Sewing cuff 116 facilitates the attachment of the heart valve prosthesis to the patient or device. Sutures, staples and/or other fastening mechanisms are passed through the sewing cuff to secure sewing cuff 116 to the patient's tissue annulus, to a conduit prosthesis or to other portions of a prosthesis. Sewing cuff 116 preferably extends outward from base 142 so that the fastening mechanism can be conveniently passed through sewing cuff 116 to attach the valve without significant risk of piercing leaflets 102, 104, 106.

For any of the prosthetic valve embodiments, suitable rigid materials for the stent include, for example, rigid polymers, metals, ceramics, carbon materials and combinations thereof. Suitable rigid polymers include, for example, polyacetals, such as Delrin® and Celcon®, polysulfones, polyethersulfones, polyarylsulfones, polyetheretherketones, and polyetherimides. Suitable metals include biocompatible metals, such as, stainless steel, titanium, cobalt alloys, such as Elgiloy®, a cobalt-chromium-nickel alloy, and MP35N, a nickel-cobalt-chromium-molybdenum alloy, and Nitinol®, a nickel-titanium alloy. Heart valve stents made from spring metals, such as Elgiloy®, exhibit good mechanical properties, such as strength and fatigue endurance, and can have a smaller cross-section than corresponding polymer stents. Composite metal/polymer heart valve stents are described in copending and commonly assigned U.S. patent application Ser. No. 09/475,721 to Reimink et al., entitled "Medical Devices With Polymer/Inorganic Substrate Composites," incorporated herein by reference. In addition, stents can be produced from ceramic materials, such as silicon carbides or metal carbides, hydroxyapatite and alumina. Suitable stents can also be produced from carbons such as pyrolytic carbon, turbostratic carbon and graphite. Composites suitable for stents that advantageously combine pyrolytic carbon and carbides are described in copending and commonly assigned U.S. patent application Ser. No. 09/460,140 to Brendzel et al., entitled "Pyrolytic Carbon and Metal/Metalloid Carbide Composites," incorporated herein by reference.

Figure 5:
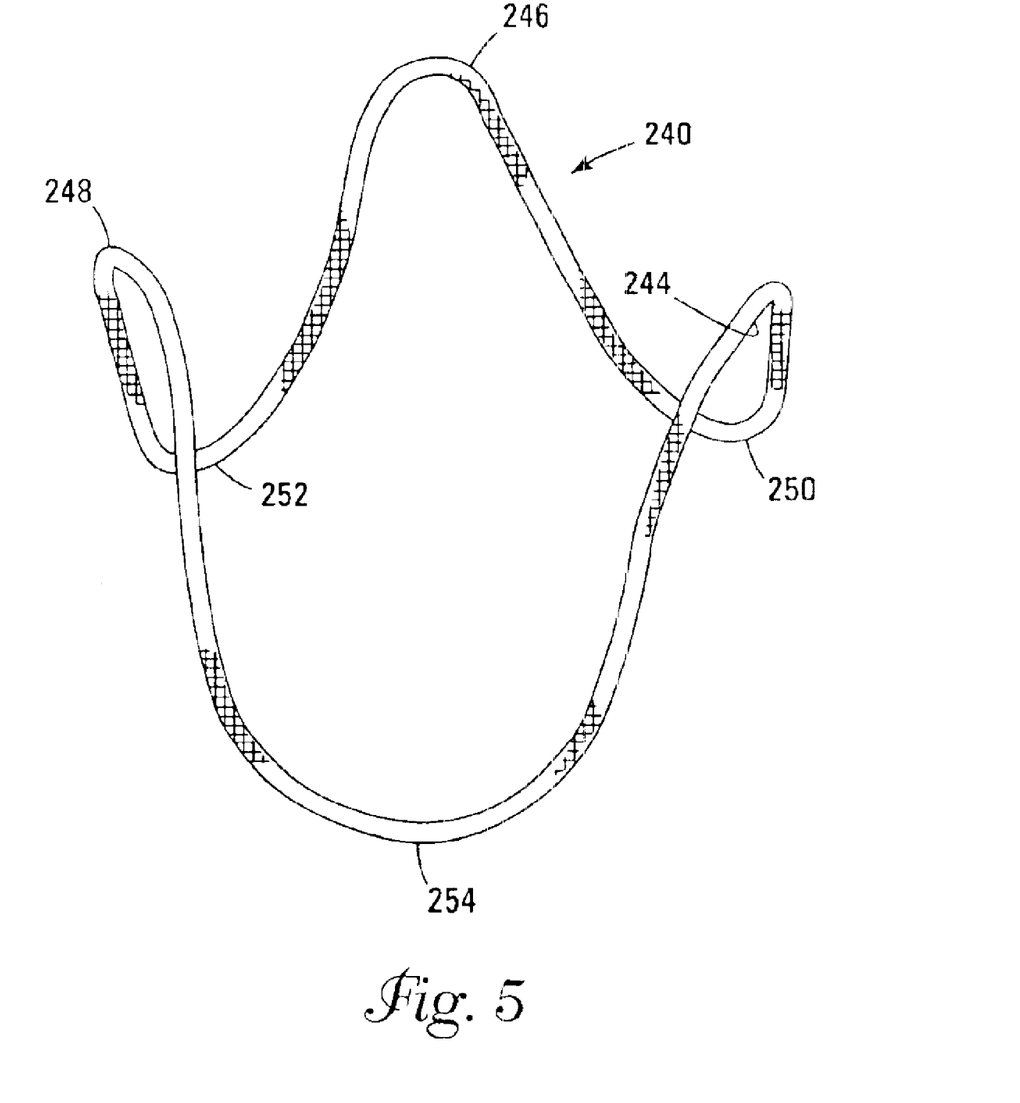
FIG. 5 is a perspective view of a wire-form stent.
Figure 6:
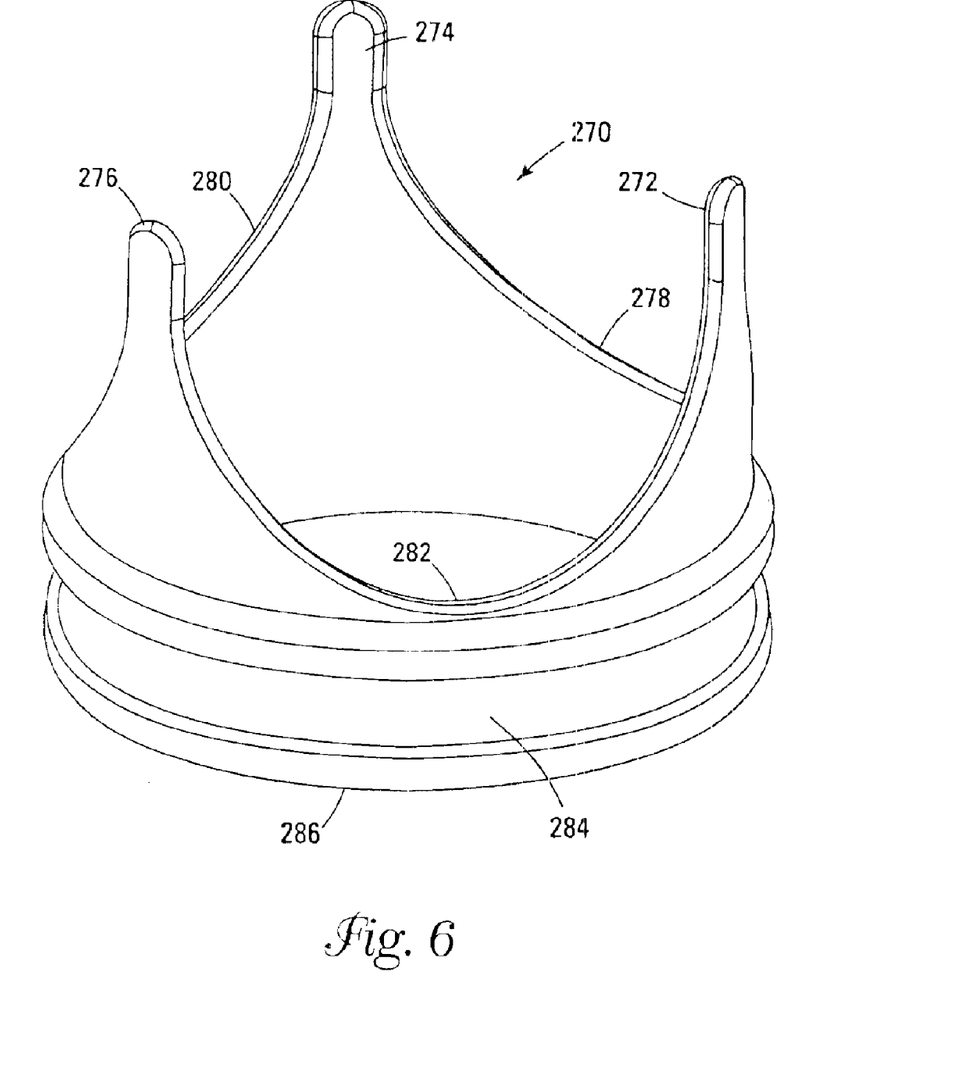
FIG. 6 is a perspective view of a sheath shaped stent.

Various embodiments of the stent structure are suitable for testing by the methods described herein. Two exemplary embodiments are shown in FIGS. 5 and 6. Referring to FIG. 5, stent 240 has a wire-form structure. Stent 240 has three commissure posts 244, 246, 248 that point generally downstream. Commissure posts are connected to adjacent posts by scallops 250, 252, 254. The wire-form structure can have various cross sectional shapes of the wire, which may or may not vary at different locations. For example, stent 240 may flatten out and thicken at the lower portion of the scallop to provide additional support for a sewing cuff or the like that is positioned near the inflow edge of the valve. A variation on this type of stent structure with a metal base ring connected to the scallops is described in U.S. Pat. No. 4,343,048 to Ross et al., entitled "Stent For A Cardiac Valve," incorporated herein by reference.

A sheath-shaped stent 270 is shown in FIG. 6. Three commissure posts 272, 274, 276 extend generally upward around the circumference of the stent. Commissure posts 272, 274, 276 are connected by scalloped portions 278, 280, 282. In contrast with the wire-form structure of the stent in FIG. 5, stent 270 has a filled in structure under commissure posts 272, 274, 276 and scallops 278, 280, 282. Stent 270 has an annular ring structure 284 at the inflow edge 286. The outer surface of stent 270 can be covered with a fabric to facilitate implantation of the valve or for convenience of handling.

Flexible leaflets are generally formed from tissue or polymers. Natural tissues are derived from a particular animal species, typically mammalian, such as human, bovine, porcine, seal or kangaroo. These tissues may include a whole organ, a portion of an organ or structural tissue components. Suitable tissues include xenografts, homografts and autografts. Synthetic tissue formed from a synthetic matrix is also possible tissue material. Tissues can be fixed by crosslinking. Fixation provides mechanical stabilization, for example, by preventing enzymatic degradation of the tissue. Glutaraldehyde, formaldehyde or a combination thereof is typically used for fixation, but other fixatives can be used, such as epoxides, diimides and other difunctional aldehydes. Particularly suitable flexible polymer materials for the formation of flexible polymer heart valve leaflets include, for example, polyurethanes, polydimethyl siloxanes, polytetrafluoroethylenes, derivatives thereof and mixtures thereof.

Sewing cuff 116 can be produced from natural material, synthetic material or combinations thereof. Suitable natural materials for sewing cuff 116 include, for example, fixed/crosslinked tissue, such as bovine or porcine pericardial tissue. Suitable synthetic materials for sewing cuff 116 include flexible polymers, generally woven into a fabric. Preferred materials include, for example, polyesters, or polytetrafluoroethylene.

Stented Structure For Testing

To test the stents under more appropriate loads and load distributions, the stents are assembled into stented test structures with a flexible material membrane supported by the stent. The stented test structures are similar to closed prosthetic valves with flexible leaflets. However, the stented test structures differ from the prosthetic valves in that the stented test structures do not open fully, if at all. The flexible membrane serves to transmit fluid pressures into loads, i.e. stresses, on the stent. If the flexible membrane has similar characteristics as corresponding leaflets and is attached to the stent in a similar way, the peak loads and distribution of loads on the stent are comparable to the peak loads and distributions of loads on the stent during actual use of a corresponding prosthesis.

By limiting the movement of the membrane such that it does not fully open in response to fluid pressures, the membrane has a significantly faster response time relative to standard valve leaflets with respect to closing upon reversal of fluid pressures. Limitations on membrane movements also reduce wear and dynamic stress relative to valve leaflets, such that the membranes generally last longer than leaflets. The limitations on the membrane opening can be structural, i.e., sealing of coaptation edges, or mechanical, i.e., reducing the flexibility of the membrane to the point at which the membrane does not fully open at the fluid pressures of the testing even though the coaptation edges are not sealed.

Similar materials can be used for the flexible membrane as are used for flexible leaflets in valved prostheses. Thus, the flexible membrane can be formed from tissue or polymer materials. In preferred embodiments, the flexible membrane has similar elasticity as corresponding flexible leaflets such that the transferred peak load is approximately the same in the prosthesis and the stented test structure. However, the flexible membrane does not need to be formed from the same material as the corresponding valve leaflets and does not need to be biocompatible since the stented test structure is not implanted into a patient. For example, it may be desirable to test a stent for a tissue-based prosthetic valve with a polymer flexible membrane.

While the flexible membrane should be somewhat flexible to respond appropriately to fluid pressures, the flexible membrane does not need to be as flexible as the prosthetic leaflets since the motion of the membrane is limited. Due to the reduced need for flexibility, a more durable material can be used for the membrane as compared to prosthetic leaflets. Thus, elasticity can be adjusted to be similar to the valve leaflets to transfer the load in an approximately equivalent manner without particular regard for the resulting flexibility of he material.

The material used for the flexible membrane should be durable since the material is used for the testing of stent fatigue. In evaluating stent fatigue, the stented test structure is cycled to simulate many years of use. For a human patient, a heart valve cycles about 40 million times each year, and the valve ideally remains functional over the remaining natural expected lifetime of the patient. In some embodiments, the flexible membrane can withstand at least about 400 million cycles and more preferably at least about 600 million cycles without significant structural deterioration. While the flexible membrane can be replaced while testing one particular stent, it is convenient to be able to use the same flexible membrane throughout the test of a single stent.

Tissue for forming a flexible membrane can be similar to the tissue used for leaflets. Glutaraldehyde crosslinked tissue can be used without concern regarding cytotoxicity or treatment with anti-calcification agents. Since flexibility is less of a concern, somewhat thicker tissue can be used. For example, bovine and equine pericardium is somewhat thicker than porcine heart valve tissue. However, tissues tend to be somewhat variable in mechanical properties.

In some preferred embodiments, the membrane is formed from polymers. Generally, any flexible polymer can be used for the flexible membrane including, for example, the same flexible polymers that are used for flexible valve polymer leaflets. A flexible polymer used to form the leaflets of heart valve prostheses is preferably a polymer that has sufficient durability to withstand the repeated cycling required for replacement heart valve use. Polyurethanes and silicone polymers are suitable polymers for forming flexible membranes that generally can achieve desired performance requirements. Since the membrane does not have to be as flexible as leaflets, the membrane can be made thicker than flexible polymer leaflets. Polymer membranes formed from polyurethane or silicone generally have a thickness from about 100 microns to about 2000 microns, and more preferably, from about 200 microns to about 500 microns. The thickness of the polymer can be adjusted to yield the approximate elasticity/extensibility of the valve leaflets to be mounted on the stent, whether tissue or polymer.

Figure 7:
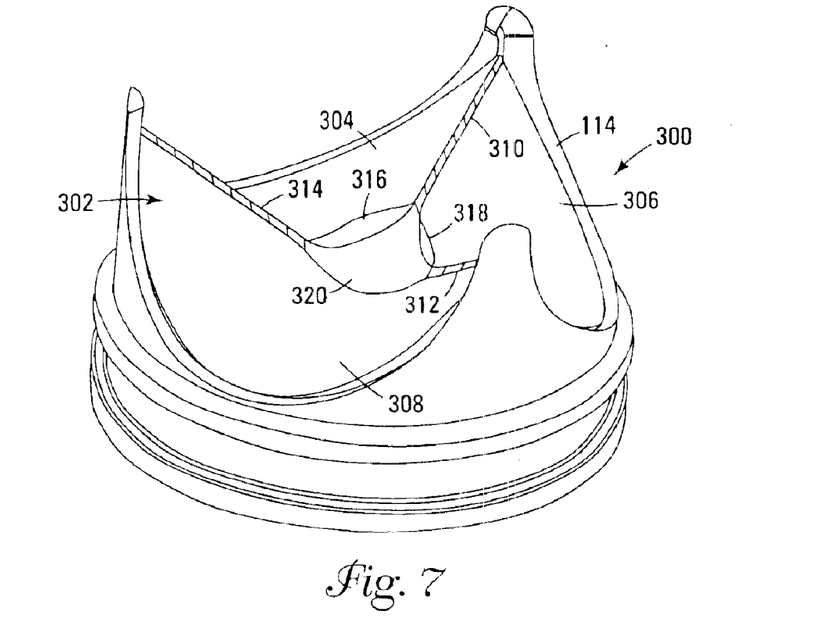
FIG. 7 is a perspective view of a stented test structure that provides for some fluid flow in the center of the valve in the forward direction.

Additionally, or alternatively, the thickness of the polymer can be increased to make the membrane less flexible such that the membrane opens a desired amount or does not open at all at the fluid pressures of the testing. The testing flexible membrane material can be more elastic so that the membrane can be thicker to match the elasticity of the leaflet while forming a stiffer, i.e., less flexible, membrane. If the membrane stiffness is large enough, the center of the membrane can open at a specific fluid pressure, such as shown in FIG. 7, while the remaining portions of the coapting edges remain closed. At even greater stiffness, the membrane does not open at all. Thus, the same effects can be achieved by selecting the stiffness without physically sealing the edges of the membrane.

Polymer membranes can include reinforcements to improve the durability of the membrane. Reinforcements can be formed as a thickening of the polymer, by the embedding of a reinforcing fiber or the like within the polymer or by a combination of a reinforcing material and a thickening. In particular, the stented test structure can include a reinforcement at the "outflow" edge of the membrane and/or along the contour of the membrane. It can be particularly advantageous to reinforce the "outflow" edge since the edge is susceptible to tearing upon repeated cycling of the stented test structure, and with the membrane, the closed portions of the membrane are susceptible to tearing to open the passage through the membrane to a larger area. In addition, reinforcements can be placed throughout the contour of the membrane or at selected locations along the contour. For example, reinforcement fibers can run parallel to the "outflow" edge or perpendicular to the "outflow" edge. The "outflow" edge is clear even if the stented test structure is sealed from flow since the membrane is shaped like leaflets that function as a one-way check valve that would open to provide flow in one direction and close to prevent flow in the opposite direction. Thus, the "outflow" edge of the membrane is the edge that corresponds in position to the outflow edge of the corresponding leaflets. Polymer heart valve leaflets are described further in copending and commonly assigned U.S. patent application Ser. No. 09/666,823 to Woo et al., entitled "Valved Prostheses With Reinforced Polymer Leaflets," incorporated herein by reference.

Tissue membranes can also be reinforced to improve durability. For example, tissue membranes can include an extra strip of tissue attached along the coaptation edge to reduce tearing of the edge. The strips can be attached with suture, staples, adhesives and the like. Non-tissue reinforcements can also be added to a tissue membrane.

The full open lumen is evaluated as the area encompassed by the largest inner circumference of the stent obtained by projecting the stent onto a plane. The plane is selected as the plane that yields the largest inner circumference of the stent. Generally, this plane is perpendicular to a central axis of the stent. In embodiments of particular interest, the flexible polymer opens only a fraction of the full open lumen when the fluid pressure is directed to opening the stented test structure. In some embodiments, the stented test structure opens between no more than about 80 percent of the full lumen, in other embodiments from about 1 percent to about 60 percent, in additional embodiments, from about 3 percent to about 50 percent, in further embodiments from about 5 percent to about 30 percent and in still further embodiments, from about 5 percent to about 20 percent of the full lumen. A person of ordinary skill in the art will recognize that ranges within theses explicit ranges are contemplated and are within the scope of the present disclosure. In other embodiments, the flexible membrane is completely closed to flow through the stented test structure.

For any membrane material, the flexible membrane in its closed configuration can approximate the shape of the closed leaflets in the corresponding valve. If the flexible membrane approximates the shape of the closed leaflets, the peak loads transferred from the fluid to the stent through the flexible membrane will more closely approximate the peak loads in the corresponding prosthesis in vivo. Then, the fatigue testing provides a more accurate evaluation of the performance of the stent in a prosthesis following implantation. The shape of the flexible membrane can approximate the shape of the closed leaflets whether or not the flexible membrane and the leaflets are formed from the same material. Similarly, the number of curved contours on the membrane generally corresponds with the number of leaflets in the corresponding valve. The orientation of the stented test structure can be referenced to the orientation of a corresponding valve manufactured from the stent. Thus, the forward direction is the direction to which the commissure posts point since the leaflets are supported by the commissure posts.

A first embodiment of a stented test structure is shown in FIG. 7. Stented test structure 300 includes stent 114 which is the stent of the prosthesis 100 of FIG. 2. Structure 300 also includes a flexible membrane 302 attached to stent 114. In a closed position, flexible membrane 302 has a similar appearance as the leaflets of FIG. 2. As shown in FIG. 7, flexible membrane 302 is in its open position. Flexible membrane 302 has three contour sections 304, 306, 308 that correspond to the leaflets of the analogous prosthesis. Contour sections 304, 306, 308 meet adjacent contours at seams 310, 312, 314. Each contour has a small free edge 316, 318, 320, respectively, at the center of membrane 302. Free edges 316, 318, 320 open in response to fluid pressures to provide some fluid flow. The respective lengths of free edges 316, 318, 320 and seams 310, 312, 314 can be adjusted to provide the desired amount of forward flow through the stented test structure as well as the response time with respect to opening and closing of the membrane. The length of free edges 316, 318, 320 correlates in a predictable manner with the size of the opening in the center of the membrane when the membrane is in an open position.

Figure 8:
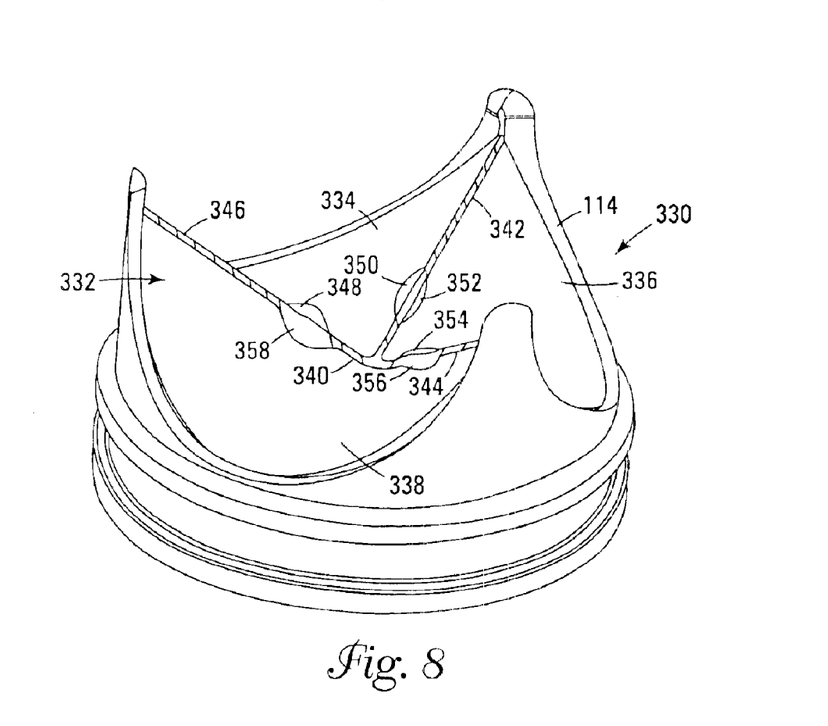
FIG. 8 is a perspective view of a stented test structure that provides for some fluid flow at three locations along seams between contours of a flexible membrane in the forward direction.

Another embodiment of a stented test structure based on stent 114 of FIG. 2 is shown in FIG. 8. Structure 330 includes a flexible membrane 332 attached to stent 114. Flexible membrane 332 has three contour sections 334, 336, 338 that correspond to the leaflets of the analogous prosthesis in FIG. 2. A central seam 340 connects contour sections 334, 336, 338 at the center of flexible membrane 332. Seams 342, 344, 346 connect adjacent contour sections away from the center of flexible membrane 332. Contour section 334 has free edges 348, 350. Similarly, contour section 336 has free edges 352, 354, and contour section 338 has free edges 356, 358.

Free edges open in response to fluid pressure to allow limited flow through the flexible membrane in the forward direction. The length of the free edges can be adjusted to yield the desired amount of flow. As shown in FIG. 8, the free edges form three openings along the edges of contour sections 334, 336, 338, roughly symmetrically distributed around the center of the contour section. More or fewer free edges can be included to correspondingly increase or decrease the number of openings for flow. For example, free edges 350, 352 can be eliminated such that there are only two openings formed by free edges 348, 358 and 354, 356. In other embodiments, additional free edges can form more than three openings when fluid pressures tend to generate forward fluid flow through the stent. For embodiments with three contours having more than three openings, there is more than one opening between two adjacent contours. Furthermore, features of the embodiments in FIGS. 7 and 8 can be combined to have free edges that open in the center of the stented test structure and free edges that open along the interfaces between adjacent contour sections. Overall, the number of free edges in the flexible membrane can yield one, two, three, four or more openings in the flexible membrane when appropriate fluid pressures are applied.

Figure 9:
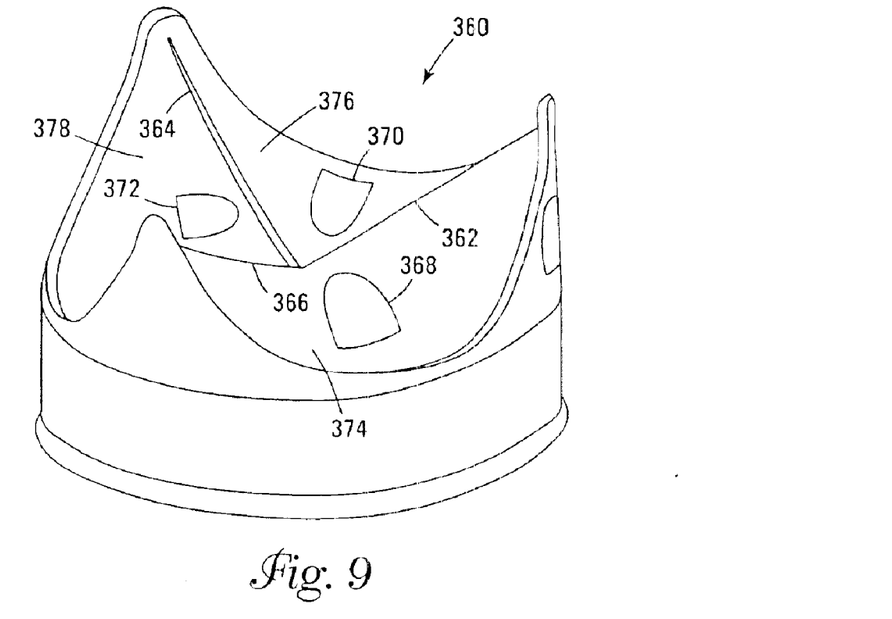
FIG. 9 is a perspective view of a stented test structure with one-way portals on the contours of the membrane of the structure.
Figure 10:
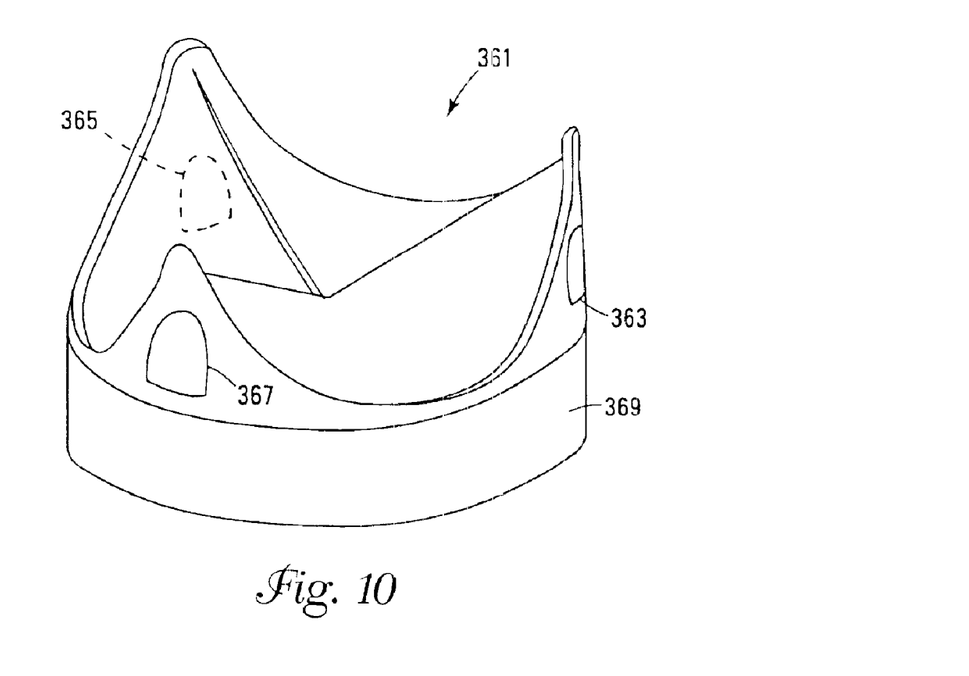
FIG. 10 is a perspective view of a stented test structure with one-way portals on the walls of the stent with one hidden portal shown in phantom lines.
Figure 11:
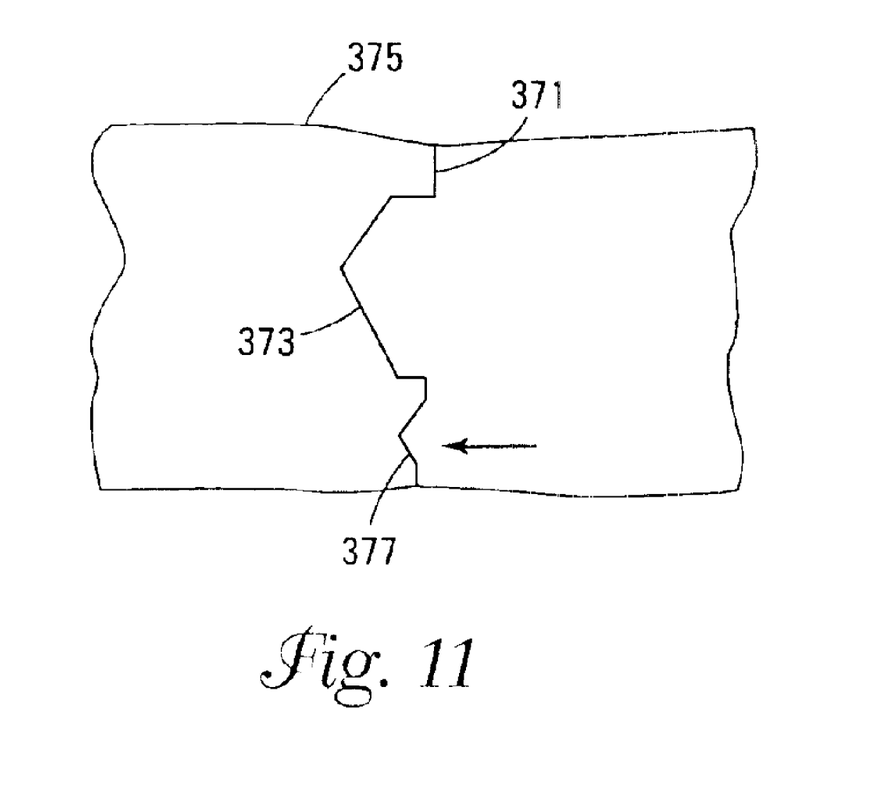
FIG. 11 is a fragmentary side view of a mount of a stented test structure with a one way check valve mounted adjacent the stented test structure to provide one-way flow past the mount.

In another embodiment shown in FIG. 9, stented test structure 360 is completely sealed along coaptation edges 362, 364, 366. Instead, one-way portals 368, 370, 372 are provided along contours 374, 376, 378, respectively, where stresses are low. Portals 368, 370, 372 flex open to provide forward flow through a hole smaller than the flap of material forming the portal. In a further embodiment shown in FIG. 10, stented test structure 361 includes portals 363, 365, 367 located on stent 369. Portals 363, 365, 367 similarly provide for one-way flow. Furthermore, one-way flow can be provided around the mount of the stented test structure of the testing apparatus. For example, as shown in the fragmentary sectional view of FIG. 11, mount 371 supports stented test structure 373 within a conduit 375. Mount 371 includes a one-way check valve 377 that provides for flow in the direction of the arrow when appropriate pressures are applied. In the embodiments of the stented test structure in FIGS. 9–11, the membrane of the stented test structure can be completely sealed, which will increase the membrane's integrity, strength and cycle life.

In general, the purpose of providing one-way flow through or around the stented test structure is to provide a more rapid equilibration of the fluid from the upstream chamber to the downstream chamber in testing apparatuses with a configuration having a fluid loop. The one-way flow compensates for upstream chamber fluid loss during the pressure loading cycle. The one-way flow is not part of the stent testing function, but can increase the testing system response speed so that the stented test structure can be tested at a higher frequency. Since the one-way flow is not part of the testing function, the one-way flow openings do not have to be associated with the membranes. The one-way flow openings can be any interface between the downstream and upstream chambers.

Figure 12:
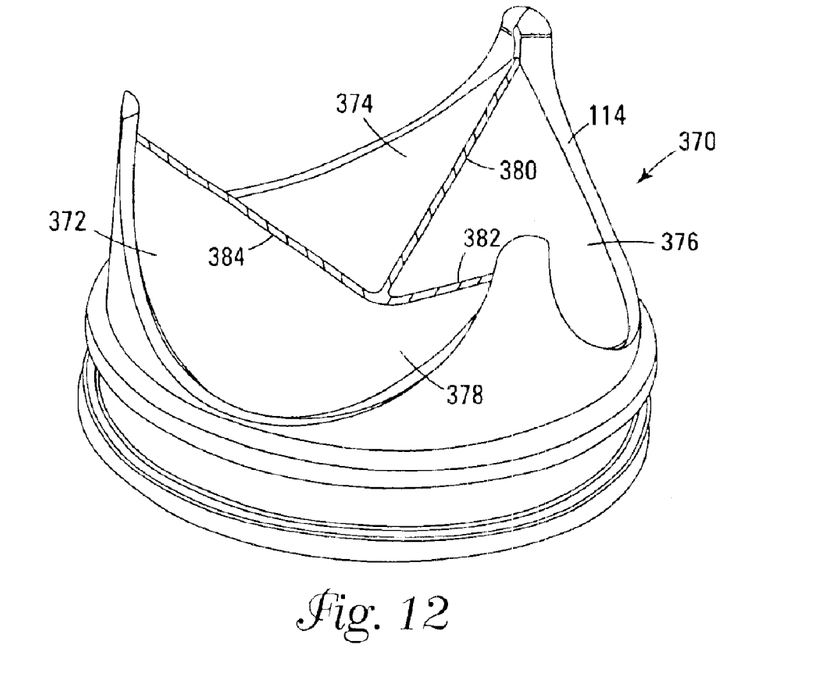
FIG. 12 is a perspective view of a stented test structure that does not provide for any flow through the stented test structure.

Another embodiment of a stented test structure incorporating stent 114 is shown in FIG. 12. Stented test structure 370 includes a flexible membrane 372 attached to stent 114. Flexible membrane 372 has three contour sections 374, 376, 378 that correspond to the leaflets of the analogous prosthesis. Seams 380, 382, 384 connect adjacent contour sections 374, 376, 378. Flexible membrane 372 does not open to allow any flow through stented test structure 370. The embodiments shown in FIGS. 7–12 corresponding to three leaflet valves can be generalized straightforwardly for embodiments with different numbers of flexible leaflets, such as two leaflets or four leaflets. All seams in FIGS. 7–12 can be formed as a sealed structure or can be fastened together for example, by suture, glue, and the like.

Desirable approaches for forming the stented test structure generally depend on the material used to form the flexible membrane. For example, flexible membranes formed from tissue materials can be sutured to the stent, or the tissue can be sutured together to form sheaths into which the stent is inserted. Additionally, or alternatively, tissue can be folded over the stent and sutured, stapled or otherwise fastened together to secure the tissue to the stent. For either tissue or polymer flexible membranes, the flexible membrane can be attached to the stent with an adhesive. Since the stented test structure is not implanted into a patient, adhesives do not need to be non-toxic or otherwise biocompatible, although surgical adhesives can be used. Generally, a particularly strong adhesive is desirable for stent testing since failure of the adhesive could delay the testing. Suitable adhesives include epoxies and polyurethane-based adhesives.

In some preferred embodiments, a polymer flexible membrane is formed directly in contact with the stent. For example, the stent can be mounted onto a mandrel contoured with the shape of the contours of the flexible membrane. Then, if the combined assembly of the mandrel and stent is dip coated, the polymer is formed around the stent and over the contours as an integral unit.

Figure 13:
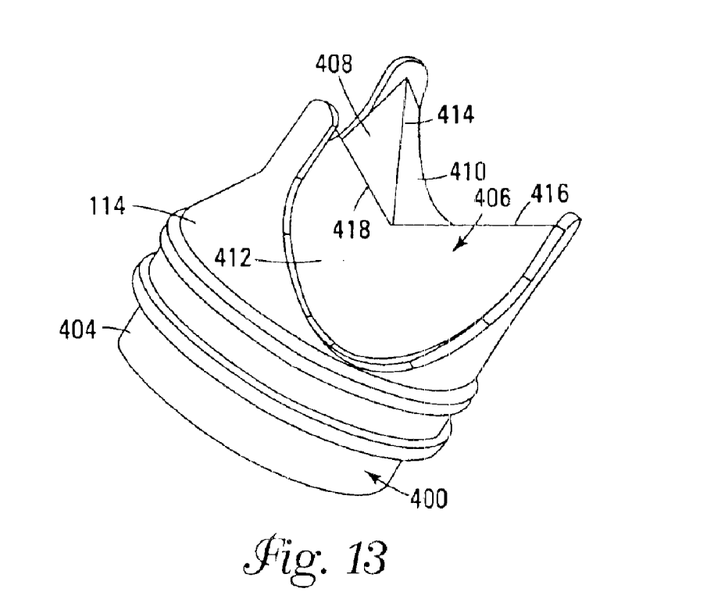
FIG. 13 is a perspective view of a mandrel with a stent mounted on the mandrel in preparation for dip coating.

A mandrel with stent 114 of FIG. 2 mounted on the mandrel is shown in FIG. 13. Mandrel 400 includes a base 404 and a contoured portion 406. The mandrel can be manually or mechanically held during the dip coating process. Base 404 can be shaped for the secure support of stent 114 during the dip coating process. Contoured portion 406 extends from base 404 and is shaped with contours to correspond with the desired flexible membrane. In particular, contoured portion 406 includes three surfaces 408, 410, 412 corresponding to the contours of the flexible membrane. Edges 414, 416, 418 separate adjacent surfaces 408, 410, 412.

In the dip coating process, the mandrel is lowered into a polymer liquid. The polymer liquid used to perform the dip coating can be a polymer solution/dispersion or a polymer melt. Suitable polymer solutions/dispersions comprise the polymer dissolved/dispersed in a solvent. The solvent can be selected based on the particular polymer. For polyurethanes, suitable solvents generally include, for example, N,N-dimethylacetamide (DMAC) and tetrahydrofuran (THF). The concentration of the solution can be selected to yield an appropriate viscosity and coating thickness. The coating thickness generally depends on the concentration and viscosity of the polymer solution. Desirable polymer concentration, i.e., solid content, generally ranges from about 1 weight percent to about 50 weight percent, and more preferably, from about 8 weight percent to about 30 weight percent, although desired values will depend on the composition of the polymer and the molecular weight of the polymer.

Polymer melts can be formed with polymers that can be heated to their melting points without decomposing. The viscosity generally will be dependent on temperature. The viscosity of the melt can be varied to obtain the desired coating thickness. Coating thickness generally is evaluated following solidification of the polymer. Desirable ranges of polymer thickness for the flexible membrane were given above.

The stent and polymer form generally are removed as a unified structure from the mandrel. The stent/polymer form can be used directly as a stented test structure or additional processing and securing can be performed. For example, the interface between the contours of the flexible membrane can be processed to further seal portions of the seam, if not adequately secured, or to cut sections to form free edges at desired locations, if formed as a seam. The mandrel shape can be machined such that selected sections are easily formed into free edges. In particular, a sharp edge placed where the free edges are desired results in free edges upon the breaking of a very weak seam that results at the sharp edge. Reinforcements can be placed along the mandrel prior to dip coating to form a reinforced polymer flexible membrane. The formation of the flexible membrane by dip coating can be adapted from processes for the formation of polymer leaflets by dip coating. The formation of polymer leaflets by dip coating is described further in copending and commonly assigned U.S. patent application Ser. No. 09/724,007 to Kurk et al., entitled "Polymer Valve Prostheses By Dip Coating," incorporated herein by reference.

Testing Apparatus

The testing apparatus includes a stented test structure, a fluid vessel with a mount for supporting the stented test structure and a cyclic pressure applicator, generally a cyclic pump, or other motorized fluid driver for applying a load to the stented test structure. If the stented test structure is sealed to prevent flow in both directions through the stent, the fluid vessel can be designed without the need for flow as long as appropriate accommodation is made for the fluid pressures during pumping such as with an appropriate reservoir. If the stented test structure allows some limited fluid flow during cycling of the valve, the fluid vessel should provide for fluid flow through the structure in the forward direction, generally by circulating the fluid through a closed loop.

It is the function of a cyclic pressure applicator or pump to apply the desired fluid pressure to the stented test structure. Peak fluid pressures generated by the pump/pressure applicator are generally in the range from about 30 mmHg to about 300 mmHg, in other embodiments from about 50 mmHg to about 250 mmHg and in further embodiments from about 60 mmHg to about 200 mmHg. These values are gauge pressures measured relative to ambient pressures of approximately one atmosphere. However, due to the frequency dependent response of the stented test structure, different fluid pressures may be used to get the equivalent stent deflection that is obtained under physiological conditions. The fluid pressure can be selected to obtain approximately the same stent deflection that is obtained under physiological pressures and cycling rates.

It is desirable to perform the fatigue testing for the stent at an accelerated rate without sacrificing the accuracy of the results. The human heart generally beats at a frequency from about 50 to about 200 cycles/beats per minute. Stent testing by deforming the stent posts generally involves 600 million cycles at about 20 Hz. Accelerated wear testers for valve leaflets generally operate in the range from about 400 cycles per minute to about 1200 cycles per minute. A cycle involves an oscillation of the pressure from a forward direction to a backward direction through a valve in a periodic or approximately periodic pattern. The testing of leaflets is limited by the response time of the leaflets to changes in fluid pressure. Since the flexible material of the stented test structure does not open up to a full open lumen, the stented test structure can be tested at frequencies generally greater than about 1000 cycles per minute, in some embodiments, from about 1200 to about 6000 cycles per minute, in further embodiments, from about 1500 to about 5000 cycles per minute, and in other embodiments, from about 2000 to about 4000 cycles per minute. A person of ordinary skill in the art will recognize that ranges within these explicit ranges are contemplated and are within the present disclosure.

Suitable fluids for applying the load generally are liquids since the fluid should be approximately incompressible over the fluid pressures experienced in the testing system. Generally, any liquid can be used that does not react with or otherwise deteriorate the flexible membrane. For stent fatigue testing, suitable liquids include, for example, saline and buffered saline with a pH near physiological pH values at 37° C. For polymer leaflets, water, other aqueous liquids and organic solvents that do not alter the polymer are generally appropriate. For sealed flexible membranes, the upstream side of the stented test structure can be exposed to air or other gas, generally at approximately atmospheric pressure, although some membrane materials, such as tissue, need to be kept moist so that liquid would be used on both sides of the membrane.

Figure 14:
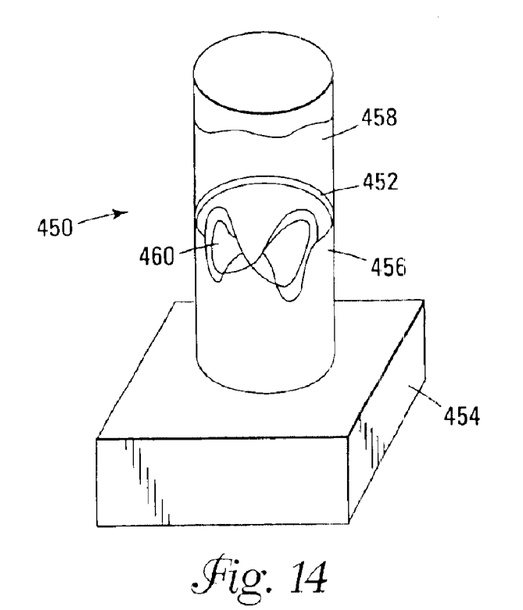
FIG. 14 is a perspective view of an embodiment of a testing apparatus that does not provide for flow through the stented test structure.

A first embodiment of the testing apparatus is shown in FIG. 14. Test apparatus 450 includes a stented test structure 452, a cyclic pump 454, a fluid conduit 456 and an optional fluid reservoir 458. In this embodiment, stented test structure 452 does not allow for flow in the forward or backward direction. There is no other fluid communication between the upstream and downstream chambers separated by the stented test structure. The cyclic pump can be any suitable pump including, for example, a piston driven diaphragm pump or other cyclic pump structure, such as a Harvard-style piston pump, a cam actuated piston pump or an electromagnetic actuator. Several of these convenient pump designs incorporate an actuator that drives a membrane or similar interface with the fluid to induce the pressure changes in the fluid. Stented test structure 452 is located within fluid conduit 456. In some preferred embodiments, fluid conduit 456 is transparent to provide for the observation of the stented test structure during the testing period. For example, fluid conduit 456 can be formed from transparent polycarbonate polymers or other polymers that can be both transparent and durable. The upstream side of the fluid conduit can be open to the air. In alternative embodiments, fluid reservoir 458 is filled with an inert gas, generally at approximately atmospheric pressure, or a volume of liquid with an expansion volume above the liquid and/or a flexible membrane to provide for pressures applied due to pump 454. Fluid reservoir 458 with liquid preferably is open to the atmosphere.

Figure 15:
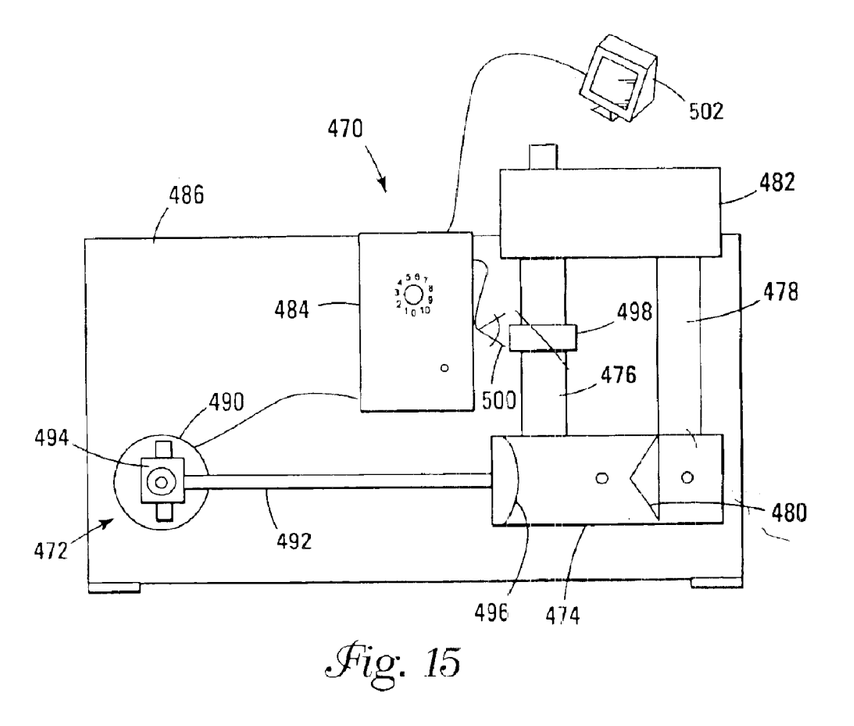
FIG. 15 is a perspective view of another embodiment of a testing apparatus that provides for optional flow through the stented test structure.

An alternative embodiment of the testing apparatus is shown in FIG. 15. Test apparatus 470 can be used whether or not flow takes place within the system. Test apparatus 470 includes a piston driven diaphragm pump 472, a pumping chamber 474, fluid conduits 476, 478, a stented test structure 480, reservoir 482 and controller 484. The components are mounted on a stand 486. Pump 472 includes motor 490, piston 492, cam 494 and a diaphragm 496 within pumping chamber 474. Cam 494 connects piston 492 with motor 490. Rotation of motor 490 moves piston 492 by way of cam 494 to pulse diaphragm 496. Adjustment of cam 494 can control the volume displacement on the diaphragm by the piston and corresponding fluid pressures on the stented test structure.

Stented test structure 480 is mounted within pumping chamber 474. Pumping chamber 474 is preferably transparent to provide for observation of the valve during operation. Fluid conduit 476 includes a flow restrictor 498 mounted within the lumen of fluid conduit 476 to provide for better control of the pressure applied to stented test structure 480. An adjustable valve can be used as flow restrictor 498. Fluid conduits 476, 478 connect and correspondingly provide fluid communication between pumping chamber 474 and reservoir 482. Reservoir 482 can have expansion volume or a flexible membrane. Similarly, reservoir 482 can be open to the atmosphere. Controller 484 can be used to control the cycle rate of diaphragm pump 472.

Test apparatus 470 can further include a camera 500, such as a digital camera and/or video camera, to facilitate measurements of post deflections. The image can be presented on a display 502 to allow for improved visual analysis of the cycling. Measurements can be made from an image of stented test structure 480 during the pumping cycle to measure maximum post deflection.

The embodiments in FIGS. 14 and 15 are exemplary of the types of testing apparatuses suitable for use in the present invention. Many variations on these structures can be constructed based on the exemplary structures shown in FIGS. 14 and 15. The apparatus in FIG. 14 includes the basic features of a testing apparatus that does not provide for flow through the stented test structure, and the testing apparatus in FIG. 15 shows the basic features of a testing apparatus that provides for optional flow through the stented test structure.

Pulsed flow can be induced in the flow systems without use of a pump that directly applies cyclic forces to the fluid. Specifically, in place of a standard cyclic pump, continuous flow pumps or physical movements of fluid-containing tubes can used to induce pulsed fluid flow. In some embodiments, a medical device is placed within a conduit that is physically moved, for example, by rotational motion to initiate fluid flow relative to the stented test structure. Periodically reversing the motion of the conduit creates the pulsed flow of the fluid. In alternative embodiments, pulsed flow is created with a continuous pump by alternatively closing valves leading to branched flow paths. Appropriately selecting a sequence for opening and closing the valves results in cyclic fluid flow. Such systems were developed to reduce blood damage in bioreactors with prosthetic valves simulating heart valve function. While in the present case there is no reason or need to use blood, these systems could be used to apply cyclic pressure to a stented test structure. These pulsed flow systems without a pulsed pump are described further in copending and commonly assigned U.S. patent application Ser. No. 09/789,130 to Lundell et al., entitled "Flow System For Medical Device Evaluation and Production," incorporated herein by reference.

Some testing of a stent was performed on a single chamber testing apparatus having many of the features shown in FIG. 15. A transparent downstream extension chamber was added to rotate the valve 90° for visual and camera access to measure post deflection. A flexible tube connected the downstream extension chamber and the upstream chamber. The upstream chamber was constructed as an open air chamber to eliminate pressure build-up at higher cycling frequencies. A DC variable speed motor was coupled to a cam linkage with a variable offset that could be adjusted to adjust the stroke. With a variable frequency and stroke volume of the diaphragm, a sinusoidal pressure waveform was generated that could be controlled in both amplitude and frequency. The magnitude of pressure waveform was adjustable to yield equivalent deflection at elevated frequencies of around 3000 RPM as the deflections observed in a pulse duplicator under standard conditions for leaflet testing. Results from the testing are described below.

Test Performance

The fatigue evaluation of a stent using the methods described herein involves forming the stented test structure and cycling the stented test structure within a testing apparatus. Formation of the stented test structure is described above. The stented fatigue test generally involves cycling the stented test structure for a predetermined number of cycles. The pressures over a cycle can be examined initially and, if desired, throughout the testing period. Visual observation of the stented test structure can be used to evaluate post deflection and the continued performance of the structure. The stent can be physically examined to evaluate stent performance especially with respect to any damage, such as fractures and/or deformations. The flexible membrane of the stented test structure can be repaired and/or replaced during the testing period if it becomes damaged.

Generally the time for a test run is determined by the total number of cycles and the frequency. For a human patient, a prosthetic valve must cycle about 40 million times each year, and the valve ideally remains functional over the remaining natural expected lifetime of the patient. Current tissue valves may require replacement following about 400 million to about 600 million cycles. Therefore, a stent preferably can withstand at least about 400 million cycles and more preferably can withstand more than about 600 million cycles without significant structural deterioration. Testing of a stent generally involves up to about 600 million cycles, although even higher numbers of cycles can be used if desired. At 3000 cycles per minute, subjecting a stent to 600 million cycles requires about 139 days.

The pump can be set to cycle the stented test structure at a desired frequency. Generally, the pressures are monitored initially to ensure that the post deflection matches the post deflections at physiological levels. Adjustments can be made to obtain stent deflection of a desired magnitude. Stent deflection can be checked through the testing period to ensure that deflection does not vary outside of desired ranges. Changes in stent deflection over time can be used to evaluate creep. Visual observation can be performed periodically to verify that the flexible membrane of the stented test structure is intact. If damage to the membrane is observed, the flexible membrane can be repaired or replaced while the testing is momentarily stopped.

The stent is generally physically examined, at least at the end of the testing period. The test can be stopped during the testing period for additional examination of the stent. If the membrane prevents observation of the stent, the stented test structure can be x-rayed to evaluate the condition of the stent without removing the membrane. Alternatively, or additionally, the flexible membrane can be removed to provide for the physical examination of the stent.

The testing procedure was tested by placing a 29 mm metallic wire frame stent covered with polyurethane in the testing apparatus, as described above. The wire-form stent was covered with a fabric and placed on a mandrel. The mandrel was contoured to produce a desired closed configuration of the resulting polymer membrane. The polymer was dip coated to produce a membrane thickness of about 0.355 microns. The coaptation edges of the membrane were unattached, but the polyurethane thickness was great enough that the contours of the membrane only opened to less than one quarter of the full open lumen during the test. The dip coating process was similar to the dip coating of mandrels to form polymer valve leaflets, as described in copending and commonly assigned U.S. patent application Ser. No. 09/724,007 to Kurk et al., entitled "Polymer Valve Prostheses By Dip Coating," incorporated herein by reference. The minimum post deflection was matched to peak post deflection measured at physiologic levels in a pulse duplicator, i.e., 200 mmHg at 5 liters per minute and 70 beats per minute. Post deflection was measured using a digital camera and image analysis software.

The embodiments above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What we claim is:

1. A method for testing a stent for a prosthetic valve, the method comprising applying fluid pressure against a stented test structure in a backward direction with the stented test structure substantially blocking the flow of the fluid, the stented test structure comprising a stent and a flexible membrane extending within a lumen defined by the stent, wherein the flexible membrane does not fully open upon application of fluid pressure in a forward direction.

2. The method of claim 1 wherein the fluid is a liquid.

3. The method of claim 1 wherein the fluid is saline.

4. The method of claim 1 wherein the fluid pressure has a peak over a cycle from about 60 mmHg to about 200 mmHg.

5. The method of claim 1 wherein:
the stent comprises a plurality of commissure posts, the flexible membrane extending between the commissure posts; and
the commissure posts deflect inward approximately an equivalent amount as the commissure posts deflect in a corresponding valve when subjected to a pulse duplicator at a physiological condition.

6. The method of claim 1 wherein the fluid pressure is cyclic.

7. The method of claim 6 wherein the cyclic fluid pressure is approximately periodic.

8. The method of claim 7 wherein the periodic fluid pressure has a frequency from about 1000 to about 6000 cycles per minute.

9. The method of claim 1 wherein the stented test structure is mounted within a conduit.

10. The method of claim 9 wherein the conduit is connected to a cyclic pressure applicator.

11. The method of claim 1 wherein the flexible membrane comprises a polymer.

12. The method of claim 11 wherein the polymer comprises polyurethane or silicone.

13. The method of claim 11 wherein the polymer is cast around the stent to form an integral unit.

14. The method of claim 1 wherein the flexible membrane comprises a tissue.

15. The method of claim 1 wherein the flexible membrane opens upon application of the fluid pressure in the forward direction no more than about 80 percent of the full open lumen at the edge of the stent corresponding to the inflow edge of the prosthesis.

16. The method of claim 1 wherein the flexible membrane opens upon application of the fluid pressure in the forward direction from about 1 percent and about 60 percent of the full open lumen at the edge of the stent corresponding to the inflow edge of the prosthesis.

17. The method of claim 1 wherein the flexible membrane opens upon application of the fluid pressure in the forward direction from about 5 percent to about 30 percent of the full open lumen at the edge of the stent corresponding to the inflow edge of the prosthesis.

18. The method of claim 1 wherein the flexible membrane forms a seal against flow in any direction through the stented test structure.

19. The method of claim 1 wherein the stent comprises a plurality of commissure posts and scallops extending between the commissure posts, and wherein the flexible membrane has a plurality of contours connecting to the stent along the scallops.

20. The method of claim 19 wherein the flexible membrane is at least partly sealed along edges between contours to restrict flow through the membrane.

21. The method of claim 19 wherein the stent has three commissure posts.

22. The method of claim 19 wherein at least one contour comprises a one way portal that provides flow upon application of fluid pressure in the forward direction and closes against fluid pressure in a backward direction.

23. A testing apparatus comprising a cyclic pressure applicator, a conduit connected to the pressure applicator, and a stented test structure mounted within the conduit to receive cyclic fluid pressures from the pressure applicator, the stented test structure comprising a stent and a flexible membrane extending within the lumen defined by the stent, wherein the flexible membrane substantially blocks flow of a fluid in a backward direction and is constrained so as not to fully open in response to fluid pressure in a forward direction.

24. The testing apparatus of claim 23 wherein the cyclic pressure applicator cycles the fluid pressures at a frequency from about 1500 to about 6000 cycles per minute.

25. The testing apparatus of claim 23 wherein the flexible membrane comprises polymer cast around the stent to form an integral unit.

26. The testing apparatus of claim 23 wherein the flexible membrane opens upon application of the fluid pressure in the forward direction no more than about 80 percent of the full open lumen at the edge of the stent corresponding to the inflow edge of the prosthesis.

27. The testing apparatus of claim 23 wherein the flexible membrane opens upon application of the fluid pressure in the forward direction from about 5 percent and about 30 percent of the full open lumen at the edge of the stent corresponding to the inflow edge of the prosthesis.

28. The testing apparatus of claim 23 wherein the flexible membrane forms a seal against flow in any direction through the stented test structure.

29. A stented test structure comprising a stent and a flexible membrane extending within the lumen defined by the stent, wherein the stent comprises a plurality of commissure posts and scallops extending between the commissure posts, and wherein the flexible membrane connects to the stent along the scallops and is constrained to open no more than about 80 percent of the full open lumen at the edge of the stent corresponding to the inflow edge of the prosthesis upon application of fluid pressure in a forward direction.

30. The stented test structure of claim 29 wherein the flexible membrane comprises a polymer.

31. The stented test structure of claim 29 wherein the polymer comprises polyurethane or silicone.

32. The stented test structure of claim 29 wherein the polymer is cast around the stent to form an integral unit.

33. The stented test structure of claim 29 wherein the flexible membrane comprises a tissue.

* * * * *